United States Patent
Hartings et al.

(10) Patent No.: US 10,813,581 B2
(45) Date of Patent: Oct. 27, 2020

(54) AUTOMATED DETECTION OF SPREADING DEPOLARIZATIONS

(71) Applicant: UNIVERSITY OF CINCINNATI, Cincinnati, OH (US)

(72) Inventors: Jed A. Hartings, Cincinnati, OH (US); Jonathan Adam Wilson, Cincinnati, OH (US)

(73) Assignee: UNIVERSITY OF CINCINNATI, Cincinnati, OH (US)

( * ) Notice: Subject to any disclaimer, the term of this patent is extended or adjusted under 35 U.S.C. 154(b) by 335 days.

(21) Appl. No.: 15/562,922

(22) PCT Filed: Jun. 30, 2015

(86) PCT No.: PCT/US2015/038427
§ 371 (c)(1),
(2) Date: Sep. 29, 2017

(87) PCT Pub. No.: WO2016/160047
PCT Pub. Date: Oct. 6, 2016

(65) Prior Publication Data
US 2018/0085047 A1 Mar. 29, 2018

Related U.S. Application Data

(60) Provisional application No. 62/141,449, filed on Apr. 1, 2015.

(51) Int. Cl.
*A61B 5/00* (2006.01)
*A61B 5/048* (2006.01)
*A61B 5/0476* (2006.01)

(52) U.S. Cl.
CPC ............ *A61B 5/4094* (2013.01); *A61B 5/048* (2013.01); *A61B 5/0476* (2013.01);
(Continued)

(58) Field of Classification Search
CPC ..... A61B 5/4094; A61B 5/0476; A61B 5/048; A61B 5/7246; A61B 5/742
(Continued)

(56) References Cited

U.S. PATENT DOCUMENTS 8,437,843 B1 5/2013 Kayyali et al.
2001/0051819 A1 12/2001 Fischell et al.
(Continued)

OTHER PUBLICATIONS

Drenckhahn et al., "Correlates of spreading depolarization in human scalp electroencephalography" (Year: 2012).*

*Primary Examiner* — Daniel L Cerioni
(74) *Attorney, Agent, or Firm* — Dinsmore & Shohl LLP

(57) ABSTRACT

Computer-implemented methods and automated systems for real-time detection of spreading depolarizations in a brain injured patient, based an algorithm of (a) providing a reference data base of spreading depolarization waveform templates generated from EEG recordings of confirmed spreading depolarizations (SD) in a reference brain-injured patient cohort; (b) recording an EEG of the brain injured patient to generate recorded EEG waveforms; (c) detecting a slow potential change present in a recorded EEG waveform by applying a power spectral density estimate to the recorded waveform; (d) comparing a detected SPC to a reference database of SD waveform template to identify a candidate SD; and (e) rejecting a candidate SD as a false positive based on overall signal power and amplitude analysis and identifying a non-rejected candidate SD as a detected SD.

14 Claims, 7 Drawing Sheets

(52) U.S. Cl.
CPC ............ *A61B 5/7246* (2013.01); *A61B 5/742* (2013.01); *A61B 5/743* (2013.01)

(58) Field of Classification Search
USPC ........................................................ 600/544
See application file for complete search history.

(56) References Cited

U.S. PATENT DOCUMENTS

| | | |
|---|---|---|
| 2005/0197590 A1 | 9/2005 | Osorio et al. |
| 2010/0049482 A1 | 2/2010 | He et al. |
| 2010/0168532 A1 | 7/2010 | Waziri et al. |

* cited by examiner

AUTOMATED DETECTION OF SPREADING DEPOLARIZATIONS

PRIORITY CLAIM

The present application claims priority under 35 U.S.C. § 119(e) to U.S. Provisional Application Ser. No. 61/141,449 filed Apr. 1, 2015 the entire disclosure of which is incorporated herein by this reference.

GOVERNMENT INTEREST

This technology was developed in part with United States government support pursuant to grant no. W81XWH-08-2-0016 from the U.S. Department of Defense, U.S. Army; the United States government may have certain rights therein.

TECHNICAL FIELD

The invention is directed to automated signal-processing methods to identify spreading depolarizations in electroencephalographic (EEG) recordings.

BACKGROUND

Spreading depolarizations are pathophysiologic waves that occur spontaneously in the brain following neurologic insults such as brain trauma or stroke. They are believed to cause further brain damage. See, for example, J. A. Hartings et al. "Spreading depolarisations and outcome after traumatic brain injury: a prospective observational study," *The Lancet Neurology*, vol. 10, no. 12, pp. 1058-1064, 2011, the entire disclosure of which is incorporated herein by this reference.

Detecting spreading depolarizations in patients is useful to identify causes of neurologic symptoms, to guide treatments, and to improve outcomes. In particular, it would be useful to detect spreading depolarization activity in real-time, since the window for initiating treatment to substantially prevent or ameliorate secondary damage due to a spreading depolarization is small in the case of many primary brain injuries. However, current practice requires manual review (visual inspection) of EEG recordings by a specially-trained expert to identify spreading depolarizations. Such expertise is not possessed by neurologists, neurosurgeons, or other clinical staff, and generally requires training certification. Furthermore, the data review software of clinical EEG systems lack the appropriate data display routines to facilitate identification of spreading depolarizations. This further limits the use of bedside depolarization monitoring, since other software may be required for off-line data analysis.

Methods for detecting spreading depolarizations by inspection of intra-cranial EEG recordings have been known, and more recently, the present investigators surprisingly discovered that through specific manipulations of the data, detecting spreading depolarizations by inspection of non-invasive scalp EEG is also possible with high degrees of sensitivity and specificity (see U.S. provisional application No. 62/035,756, the entire disclosure of which is incorporated herein by this reference). Yet the development of a clinically useful automated detection process that may be utilized in a real time frame for all brain-injured patients has been elusive due in part to the difficulty in developing an algorithm able to deal effectively with false positives while minimizing false negatives. Further, due in part to the subjective nature of data/waveform analysis, an automated algorithm must include an ability by the user to interact with the output, to tailor output parameters, and to update and query the system.

Currently patients and clinical care-givers must rely on the presence and availability of a specially trained EEG expert. Where multiple brain-injured patients are involved, the personnel and time deficiencies of the current standard can be seriously compromising to effective treatment of brain-injured patients. Clearly, automated methods and systems effective for detecting spreading depolarizations in real time at the point-of-care of a brain-injured patient remain a critical need in the art.

SUMMARY

Accordingly, the present disclosure provides systems and methods for identifying/detecting spreading depolarizations in EEG recordings through an automated computational algorithm that may be applied at the bedside in real-time for patient care. In some embodiments the EEG waveform recording database consists of intracranial EEG recordings from brain-injured patients, and in other embodiments the EEG waveform database consists of scalp EEG recordings from brain-injured patients. Demonstration of functional implementation and utility are performed with a corresponding EEG recording.

General embodiments of an automated computational algorithm/procedure effective to identify depolarization events in a brain-injured patient comprise: 1) detecting slow potential changes (SPCs) using a power spectral density estimate, for example an autoregressive estimate; 2) matching detected SPC to a database of spreading depolarization EEG waveforms (i.e., template matching) derived from EEG waveforms of confirmed spreading depolarization (SD) waveforms; 3) rejecting false positives based on analysis of signal power and amplitude; and 4) testing for depression of high-frequency power during the suspected SD.

One embodiment provides an automated algorithm for real-time detection of spreading depolarizations in a brain injured patient. According to some embodiments, the methods comprise: (a) providing a reference data base of spreading depolarization (SD) waveform templates generated from EEG recordings of confirmed spreading depolarizations in a reference brain-injured patient cohort; (b) recording an EEG of the brain injured patient to generate recorded EEG waveforms; (c) detecting a slow potential change (SPC) present in a recorded EEG waveform by applying a power spectral density estimate to the recorded waveform; (d) comparing a detected SPC to a reference database of SD waveform template to identify a candidate SD; and (e) rejecting a candidate SD as a false positive based on overall signal power and amplitude analysis and identifying a non-rejected candidate SD as a detected SD; wherein steps (a) through (e) are implemented on a computer.

Another embodiment provides automated systems for detection of a spreading depolarization in a brain-injured patient. In some embodiments the systems comprise: a) an EEG device comprising at least 8 electrodes, a recording device, and a display device; b) a control computer comprising i) a database of reference EEG waveform templates indicative of a spreading depolarization; ii) EEG software coding for capturing and, optionally, storing one or more waveforms recorded from the EEG device over a detection period; iii) EEG waveform analysis software coding for comparing captured waveforms to the database of reference EEG waveform templates, and analyzing whether a spreading depolarization is present in the captured waveform; and iv) utility software coding for user interactive functionality; and c) an interactive user interface; wherein system components a, b and c are operationally linked.

Other embodiments provide automated methods for treating a brain-injured patient, the methods comprising: utilizing an embodiment of the automated system according to record and assess an EEG of the brain injured patient in order to detect a spreading depolarization that may be present; and initiating a treatment of the patient effective to decrease one or both of frequency and duration of a spreading depolarization upon detection of a spreading depolarization.

Automated clinical methods for rapid triage of brain-injured patients by detecting spreading depolarizations are also contemplated by effectuating an embodiment of the automated algorithm and assigning a greater urgency to patients exhibiting a detected SD over patients not exhibiting a detected SD, and a greater urgency to patients exhibiting a propagating SD over patients not exhibiting a propagating SD.

These and other embodiments will be elaborated and clarified by reference to the following figures and detailed description, including examples. Figures and examples are set forth to illustrate particular aspects and embodiments, and should not be construed as limiting the full scope of the claims appended hereto.

DETAILED DESCRIPTION

Figure 1:
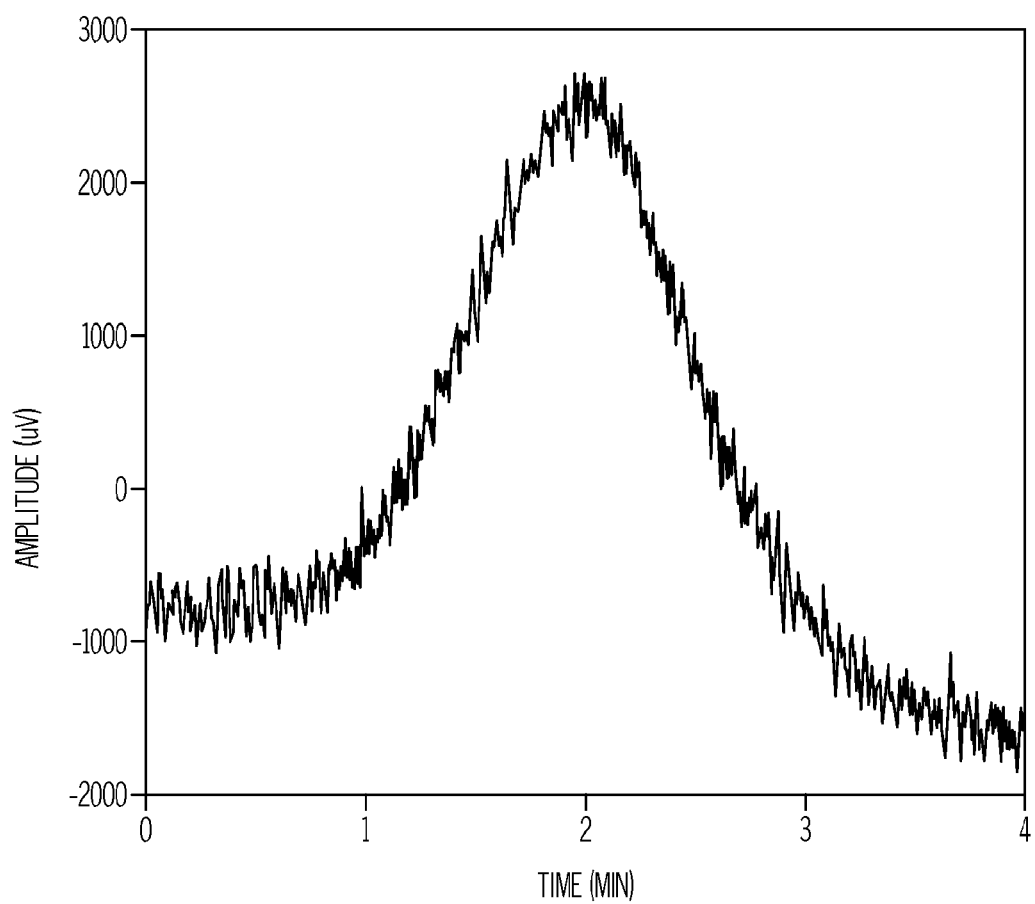
FIG. 1. Graphical representation of a spreading depolarization EEG waveform

Particular details of various embodiments of the invention are set forth to illustrate certain aspects and not to limit the scope of the invention. It will be apparent to one of ordinary skill in the art that modifications and variations are possible without departing from the scope of the embodiments defined in the appended claims. More specifically, although some aspects of embodiments of the present invention may be identified herein as preferred or particularly advantageous, it is contemplated that the embodiments of the present invention are not necessarily limited to these preferred aspects.

Unless defined otherwise, all technical and scientific terms used herein have the same meaning as commonly understood by one of ordinary skill in the art to which the presently-disclosed subject matter belongs.

A general embodiment of an algorithm developed for automation includes several analysis steps including: 1) detecting slow potential changes (SPCs) using a power spectral density estimate, for example an autoregressive estimate; 2) matching detected slow potential changes to a waveform database consisting of spreading depolarization waveforms; 3) rejecting SPC-like waveforms in the recordings that are not caused by spreading depolarizations based on overall signal power and amplitude; and 4) testing for depression of high-frequency power during the suspected spreading depolarization.

One embodiment is directed to an automated algorithm for real-time detection of spreading depolarizations in a brain injured patient. By "real-time," it is meant that input data is processed within milliseconds to seconds and output is generated virtually immediately as feedback. The algorithm comprises: (a) providing a reference data base of spreading depolarization (SD) waveform templates generated from EEG recordings of confirmed spreading depolarizations in a reference brain-injured patient cohort; (b) recording an EEG of the brain injured patient to generate recorded EEG waveforms; (c) detecting a slow potential change (SPC) present in a recorded EEG waveform by applying a power spectral density estimate to the recorded waveform; (d) comparing a detected SPC to a reference database of SD waveform template to identify a candidate SD; and (e) rejecting a candidate SD as a false positive based on overall signal power and amplitude analysis and identifying a non-rejected candidate SD as a detected SD; wherein steps (a) through (e) are implemented on a computer.

In the context of EEG recordings, investigators have determined an SD is characterized by a depression in high frequency power/amplitude at a channel when compared to a baseline recording for a patient. In the case of the automated algorithm, the recorded EEG wave form is compared to a reference waveform template. In specific embodiments, the algorithm further comprises (f) testing a detected SD for depression of high-frequency power and identifying a detected SD as an SD with depression if depression of high-frequency power is observed. In very specific embodiments (f) comprises: (i) calculating a mean high-frequency power in a time frame prior to a template marker; (ii) calculating a mean high-frequency power in a time frame subsequent to the template marker; (iii) calculating a ratio of (i) to (ii); and (iv) identifying a detected SD as a detected SD with depression if the ratio is <0.66.

An important issue when using AR estimates is selecting an appropriate model order: if the order is too small, the model does not adequately represent the signal, while too large of a model will result in over-fitting the signal, producing a noisy estimate, and requiring more computation time. As set forth in Example 3, an AR model order of 20 was eventually selected and able to find the relevant peaks in the SD frequency range. Signal artifacts may be detected and rejected. For example, according to one specific embodiment, the total signal power is between 10 $\mu V^2$ and 30 $\mu V^2$ across a 30 second window, and if the total signal power is greater than 30 $\mu V^2$ then it is rejected as signal artifact and no further analysis is performed within the 30 second window.

According to particular embodiments, a recorded EEG waveform is identified as a detected SPC if, upon application of the AR power spectral density estimate, the recorded EEG waveform exhibits a peak between 0.004 Hz and 0.009 Hz, within a period of 110-250 seconds, with a peak power and a power ratio R1>1.5 and a power ratio R2>5, wherein R1 is a ratio of the peak power to power in a neighboring lower frequency band and R2 is a ratio of the peak power to power in a neighboring higher frequency band, as illustrated in Example 3.

Once an SPC is detected, it may be compared to a reference database of SD waveform templates to identify a candidate SD. In specific embodiments, correlative analysis is applied, for example, a coefficient of correlation between a detected SPC and a reference waveform database template is scored and determined to be a candidate SD if the coefficient of correlation $r^2 > 0.95$, as illustrated in Example 4. In some embodiments, if $r^2$ is <0.95, it may be marked as an unlikely SD, but still saved for further potential analysis.

The power ratio analysis does not consider the magnitude of the power spectral peaks, however, and the template correlation analysis compares normalized waveforms. Thus, very large and very small SPCs that may look like SDs result in false positives. Therefore, the peak-to-peak values of the SD wave are measured to determine if the amplitude is appropriate, as illustrated in Example 5. In certain specific aspects a candidate SD is rejected as a false positive if a calculated peak-to-peak value of the candidate SD is measured as less than 500 μV or greater than 35 mV.

Propagation is a characteristic feature of a spreading depolarization. Where a depolarization spreads, a waveform feature indicative of spreading depolarization, such as the depression in high frequency amplitude, may be detected with a time delay between two or more channels. In some embodiments, where an SD is detected on a neighboring electrode within a relevant time frame, then the detected SD and the detected neighboring SD are classified as propagating from a same event. A relevant time frame may vary according to the size or age of a brain-injured patient, or the extent/type of the primary injury. In very specific embodiments, if the detected neighboring SD occurs within eight (8) minutes of the detected SD, the SD is classified as propagating. Generally a detectably propagating depolarization is more likely to result in secondary injury than when propagation is not detected; however the latter case may still be a valid SD.

In some embodiments a detected SD is assigned a confidence classification and one or more notification thresholds may be set for notifying a clinician of a detected SD. For example, a confidence classification may be set higher or lower depending on whether the primary injury is known to frequently be accompanied by secondary injury. In other examples a series of thresholds may be set as a means for triaging patients, or for making decisions about additional testing or interventions. Once an SD is detected, a confidence notification may also be used to determine whether the SD waveform will be added to the reference SD waveform template database.

Although the exemplary data was generated using intracranial EEG, the present investigators recently developed novel methods for detecting spreading depolarizations using scalp EEG (U.S. provisional application No. 62/035,756, the entire disclosure of which is incorporated herein by this reference). The presently inventive subject matter may therefore be based on either intracranial EEG or scalp EEG, depending on the needs of the patient and clinician.

Other embodiments are directed to automated systems for detection of a spreading depolarization in a brain-injured patient comprising: a) an EEG device comprising at least relevant number of electrodes, a recording device, and a display device; b) a control computer comprising i) a database of reference EEG waveform templates indicative of a spreading depolarization; ii) EEG software coding for capturing and, optionally, storing one or more waveforms recorded from the EEG device over a detection period; iii) EEG waveform analysis software coding for comparing captured waveforms to the database of reference EEG waveform templates, and analyzing whether a spreading depolarization is present in the captured waveform; and iv) utility software coding for user interactive functionality; and c) an interactive user interface; wherein system components a, b and c are operationally linked. What constitutes a relevant number of electrodes is determinable by the clinician based on the age/size of the patient, the extent of the primary injury, and location of the primary injury. Generally, the number of electrodes is determined by the manufactures and extraneous electrodes are not problematic. According to very specific embodiments, the EEG device includes a minimum of 7 electrodes, for example six electrodes and one reference electrode, or it includes a minimum of 8 electrodes.

Figure 4:
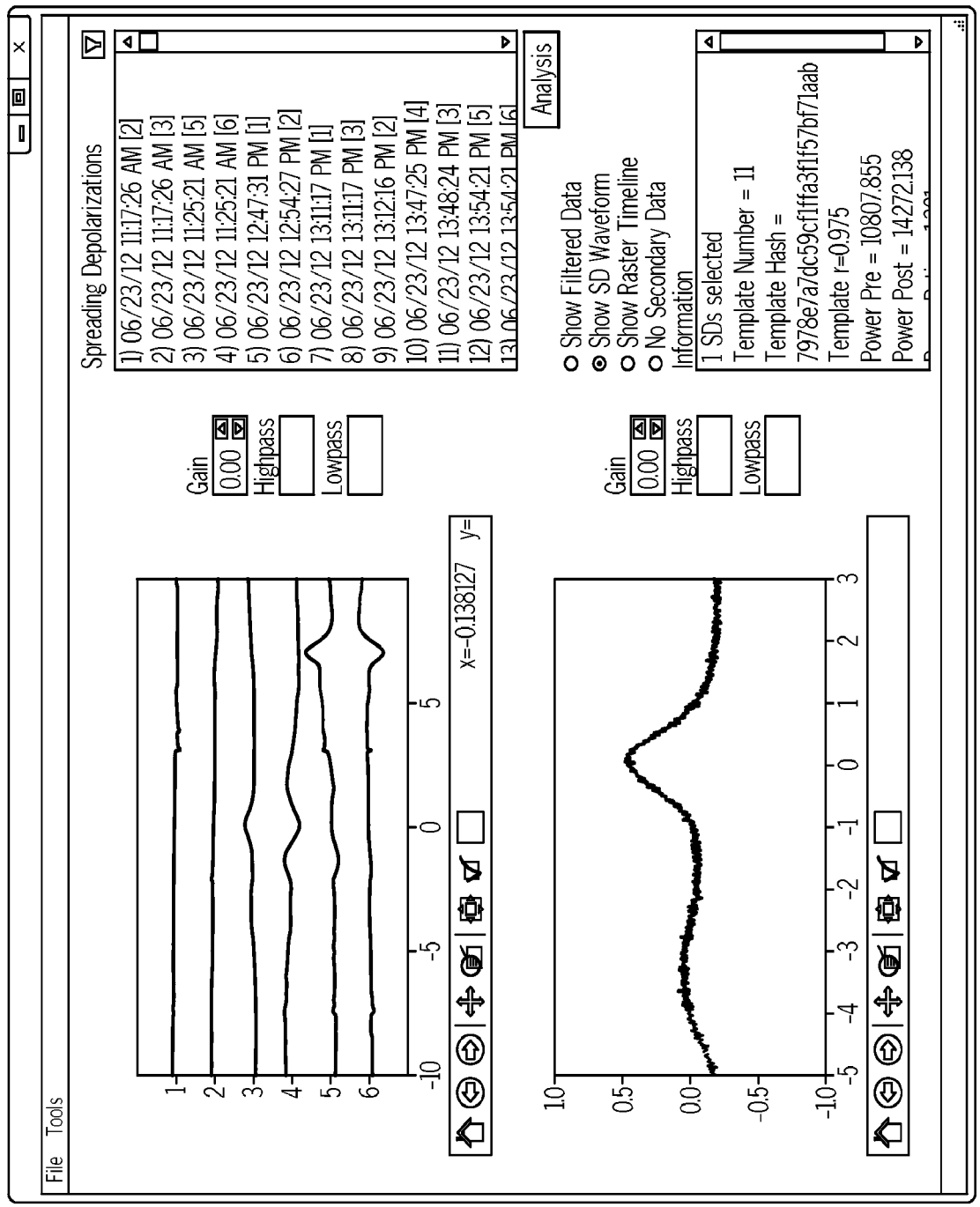
FIG. 4. Spreading polarization analysis tool; software reads detected waveform segments from the binary data file, and displays a list of all SD events. Illustrates one embodiment of how data for all EEG channels are displayed, as well as a zoomed view of the detected waveform and/or high-frequency data.

In some embodiments the interactive user interface comprises a display screen and a user input device. Interactive functionality may include one or more of marking, flagging, and classifying waveforms, and/or manually adding/deleting waveforms to or from the waveform database, and creating new waveform templates. An example of one embodiment of a computer display in accordance with the system is illustrated by FIG. 4, which sets forth SD analysis software tools, and FIG. 5, which illustrates and SD waveform database tool (see Example 9).

Embodiments providing methods for treating brain-injured patients are also contemplated. These methods utilize embodiments of automated system to record and assess an EEG of the brain injured patient in order to detect a spreading depolarization according to embodiments of the inventive algorithm. If one or more spreading depolarizations are detected, treatment is initiated. Treatment may include treatment of primary injury or treatment to prevent or contain secondary injury. A suitable treatment may be selected by the clinician based on the nature and cause of the primary brain lesion or insult to the patient's brain. Causes of lesions known to be frequently accompanied by spreading depolarizations include ischemic brain injury, hemorrhagic brain injury, or traumatic brain injury. Further, a suitable treatment may be directed or supplemented by direct treatment of the brain to inhibit spreading depolarizations. Generally, spreading depolarizations are known to decrease brain concentrations of inhibitory neurotransmitters such as gamma-amino butyric acid and serotonin. This makes the brain more vulnerable to seizure activity and other conditions associated with CNS excitability. Non-limiting examples of neuroprotective therapies which may reduce spreading depolarizations include administering one or more of an N-methyl-D-aspartate receptor antagonist, magnesium, a voltage-sensitive calcium channel antagonist, an inhibitory neurotransmitter receptor agonist or re-uptake inhibitor, an antioxidant, a free radical scavenger, caffeine with or without ethanol, estrogen, progesterone, ginssenoside, selegiline and nicotine; and/or instigating hypothermia. Administration of agents effective to increase brain concentration of inhibitory neurotransmitters, including serotonin and gamma-amino butyric acid, may be particularly effective in protecting the brain against secondary injury due to spreading depolarizations.

Treatment may be monitored for efficacy by running a continuous EEG utilizing the system and detecting any difference in the frequency, duration, or extent of spreading depolarizations.

The automated system and methods disclosed herein lend themselves conveniently to triage of brain-injured patients.

The ability to provide real-time, point-of-care triage is particularly useful in military and disaster situations or responses. Greater urgency may be assigned to a patient based on detection of SD activity, or based on particular features of SD activity, such as frequency, duration and propagation.

The automated system and methods disclosed herein provide a sensitive and selective capability for detecting spreading depolarizations. In very specific embodiments, the detection according to the disclosed methods has greater than 80% selective and greater than 90% sensitive for detection of spreading depolarizations (see Example 10 and Table 1).

Software aspects of the inventive system may be stored on a non-transitory computer-readable storage medium bearing executable code for executing embodiments of the algorithm and other system functionality as described herein.

The following examples are set forth to illustrate particular aspects and embodiments disclosed and claimed herein, and to guide the practitioner to practice the invention as defined by the claims. The examples should not be construed as limiting of the full scope of the claims as appended hereto.

EXAMPLES

Example 1. Data Collection

Intracranial EEG data were amplified and digitized with a g.USBamp (g.tec, Graz, Austria), a 24-bit direct current ADC. The data were digitized at 1200 Hz per channel, and recorded on a PC or laptop computer using the COSBID M3 software system (set forth in detail in J. A. Wilson, et al. "COSBID-M3: A Platform for Multimodal Monitoring, Data Collection, and Research in Neurocritical Care," *Acta neurochirurgica. Supplement*, vol. 115, pp. 67-74, January 2013, the entire dislosure of which is incorporated herein by this reference).

Example 2. Automated Detection Algorithm in Computer-Executable Code

The EEG data were analyzed using custom software written using a combination of C++, Python, and Matlab. Generally the algorithm includes several analysis steps including: 1) detecting slow potential changes (SPCs) using a power spectral density estimate, for example an autoregressive estimate; 2) matching detected slow potential changes to a waveform database consisting of spreading depolarization waveforms; 3) rejecting SPC-like waveforms in the recordings that are not caused by spreading depolarizations based on overall signal power and amplitude; and 4) testing for depression of high-frequency power during the suspected spreading depolarization.

Illustrative embodiment of embodiment of the algorithm as computer-executable code:

```
SDARanalysis.m
% last edited by Jonathan Wilson
function SDmap = SDARanalysis(fname, devNum)
% read the data source header information
fid = fopen(fname, 'rb');
hdr = readLCHeader(fid);
% determine whether to use the GPU
if devNum > 0
useGPU = gpuDeviceCount;
else
useGPU = 0;
end
if ~exist('devNum','var')
devNum = 1;
end
if useGPU > 0 && devNum > 0
%gpuDevice(devNum);
end
%% load the spreading depression waveform templates
templates = loadTemplatesHDF5('../sddb.hdf5');
%% setup variables
fs = hdr.samplingRate; % input sampling rate
mOutFs = 2; % analysis sampling rate
DS = floor(fs/mOutFs); % downsample factor
updatePeriodRaw = fs*30; % sliding window step size - 30 seconds
SDbufferTime = 4*60; % amount of data in the buffer
SDnumWindows = 8; % the number of windows in the buffer
SDsampleBlockSize = SDbufferTime/SDnumWindows*mOutFs;
blocksUntilTemplate = 2;
corrBufSize = 6*60*mOutFs; % amount of data in the correlation buffer
sendBufferSize = 20*60*mOutFs; % total size of data blocks to save
preSDdur = 8*60*mOutFs; % amount of data to save prior to SD detection
SDbuffer = zeros(SDbufferTime*mOutFs, 6); % data buffers
PBuffer = zeros(sendBufferSize, 6);
sendBuffer = zeros(sendBufferSize, 6);
% read one sample block at a time
blockSize = hdr.nChannels*updatePeriodRaw;
curT = datenum(hdr.year, hdr.month, hdr.day, hdr.hour, hdr.minute, hdr.seconds);
SDmap = { };
SDkeep = { };
sampleNum = 1;
%% setup filters
[Baa, Aaa] = butter(2, [0.5 20]/fs*2,'bandpass'); % the high-frequency filter
[B2,A2] = butter(2,0.02/fs*2); % low-frequency filter
[~,Zf] = filter(Baa, Aaa, zeros(10,6)); % initial conditions
[~,Zf2] = filter(B2,A2,zeros(10,6));
```

```
%% read data from the file
while ~feof(fid)
% read data into a buffer and reshape it, keeping only the 6 ECoG channels
[buf, nEls] = fread(fid, blockSize,'float32');
buf = reshape(buf,hdr.nChannels,[ ])';
buf = buf(:,1:6);
curT = curT + (size(buf,1)/fs)/86400;
% filter the data to calculate the power (pBuf = power buffer)
[pBuf, Zf] = filter(Baa,Aaa,buf, Zf,1);
% square the power, and decimate it
pBuf = decimate_gpu(pBuf.^2, DS);
% decimate the raw buffer; no need to downsample, since it uses a rolling average
buf = decimate_gpu(buf, DS);
% copy data back from GPU
buf = double(gather(buf));
pBuf = double(gather(pBuf));
% calculate the mean of pBuf over this 30s window
MP = mean(pBuf,1);
% valid channels have are in [10 uV2 and 5e5 uV2]
goodChs = MP > 10 & MP < 5e5;
% update the circular buffers with new data
SDbuffer = [SDbuffer(length(buf)+1:end,:); buf];
PBuffer = [PBuffer(length(pBuf)+1:end,:); pBuf];
sendBuffer = [sendBuffer(length(buf)+1:end,:); buf];
% calculate the power using an autoregressive power spectral density estimate
PSD = ARpower(SDbuffer, mOutFs, useGPU);
% calculate the power ratios at different frequencies
[ratios] = getPowerRatios(PSD, goodChs);
% these ratios determine which channels have slow potential changes, the first step↓
    in detecting SDs
% chsWithSPC are the list of channels with SPCs
chsWithSPC = getChsWithSPC(ratios);
% this is slightly confusing - we check the template correlations with any detected↓
    SPCs
% from the PREVIOUS loop - potential SDs are stored in SDmap, and new SPCs are↓
    returned in newSD
[SDmap, newSD] = checkCorr(SDmap, sendBuffer,templates, corrBufSize, useGPU,
fs,↓
    blocksUntilTemplate*SDsampleBlockSize);
% for newly detected SPCs, we check for depressions in the power buffer
for i=1:length(newSD)
nsd = newSD(i);
% we keep track of ALL SPCs, even those that are rejected, for↓
    sensitivity/electivity analysis
% that is, all potential events are saved
SDmap{nsd} = checkDepression(SDmap{nsd}, PBuffer(:, SDmap{nsd}.channel),↓
corrBufSize);
end
if isempty(chsWithSPC)
% if no channels have SPCs this iteration, continue with the next block
sampleNum = sampleNum + length(buf)*DS;
continue;
end
% iterate over all channels with SPc
for ch=1:length(chsWithSPC)
% create a new SPC event object
psdW = getPSDwidth(PSD(:,chsWithSPC(ch)));
spc = createNewSPC(SDbuffer, PSD, chsWithSPC(ch), curT, ratios);
spc.blocksUntilTemplate = blocksUntilTemplate;
spc.fs = mOutFs;
spc.fname = fname;
spc.sample = sampleNum;
spc.psdW = psdW;
SDmap{end+1} = spc;
end
sampleNum = sampleNum + length(buf)*DS;
end
%
fclose(fid);
end
%===========================================================
======
function arr = ARpower(buf, mOutFs, useGPU)
if useGPU
ARparms.startFreq = 0;
ARparms.endFreq = 0.013;
ARparms.evalsPerBin = 32;
ARparms.binWidth = 0.0001;
ARparms.fs = mOutFs;
```

```
[arr, ~, A] = ARpower_gpu(buf, 20, ARparms);
else
w=0:0.0001:0.013;
arr = zeros(length(w), 6);
parfor i=1:size(buf,2)
arr(:,i) = pburg(buf(:,i)-mean(buf(:,i)), 20, w, mOutFs);
end
end
end
%================================================================
======
function [ratios] = getPowerRatios(PSD, notEmptyCh)
ratios=[ ];
prng1 = 30;
prng2 = 90;
trng1 = 1;
trng2 = 11;
trng3 = 119;
trng4 = 130;
m = max(PSD);
for i=1:size(PSD,2)
if ~notEmptyCh(i)
continue;
end
ratios{i} = [ ];
a=find(PSD(:,i)==m(i));
if isempty(a) || a(1) < prng1 || a(1) > prng2
continue;
end
a=a(1);
try
pk1 = mean(PSD([-2:2]+a, i));
pk2 = mean(PSD(trng1:trng2, i));
pk3 = mean(PSD(trng3:trng4, i));
catch
asdf=1;
end
ratios{i} = [pk1 pk2 pk3];
end
end
%================================================================
======
function psdW = getPSDwidth(psd)
a= find(psd==max(psd));
v=psd(a);
a2=find(psd(1:a) < v*0.66);
if isempty(a2)
a2=1;
end
a3=find(psd(a:end) < v*0.66)+a-1;
if isempty(a3)
a3 = length(psd);
end
psdW = a3(1)-a2(end);
end
%================================================================
======
function chs = getChsWithSPC(ratios)
chs=[ ];
for i=1:length(ratios)
R = ratios {i};
if isempty(R) continue; end
pr1 = R(1)/R(2);
pr2 = R(1)/R(3);
if pr1 >= 1.5 &&...
pr2 >= 3 &&...
pr2 > pr1
chs = [chs; i];
end
end
end
%================================================================
======
function spc = createNewSPC(SDbuffer, PSD, ch, timestamp, ratios)
spc.SPCwave = SDbuffer(:,ch);
spc.PSD = PSD(:,ch);
spc.channel = ch;
spc.timestamp = timestamp;
spc.ratios = ratios {ch};
```

```
spc.corrTested = 0;
spc.deprTested = 0;
spc.classify = 0;
end
%================================================================
======
% check correlation values for each SPC, and accept or reject it based on
% how well it matches one or more templates
function [SDmap, newSD] = checkCorr(SDmap, sendBuffer,templates, len, useGPU,
trueFs,↓
    blockDelay)
toRemove = [ ];
newSD = [ ];
for i=1:length(SDmap)
if SDmap{i}.corrTested continue; end
spc = SDmap{i};
spc.blocksUntilTemplate = spc.blocksUntilTemplate-1;
if spc.blocksUntilTemplate >= 0
SDmap{i} = spc;
continue;
end
ch = spc.channel;
buf = sendBuffer(length(sendBuffer)-len+1:end,ch);
[CC,IDX,spcWave, amps, maxTemplate] = getMaxCorrelation(buf, templates, spc.fs,
0.93,↓
    useGPU);
IDX = double(IDX);
spc.corrTested = 1;
if ~isempty(CC)
if (abs(CC) > 0.93)
spc.templateCC = CC;
spc.templateHash = templates{maxTemplate}.name;
spc.SPCwave = spcWave;
spc.spcAmp = amps;
spc.corrIdx = IDX;
dS = (IDX - blockDelay)/spc.fs*trueFs;
spc.sample = spc.sample + dS;
spc.templatePoints = round(double(templates{maxTemplate}.wavePoints)/
(templates{maxTemplate}.samplingRate/spc.fs));
spc.timestamp = spc.timestamp + (IDX - blockDelay)/spc.fs*1/(60*60*24);
SDmap{i} = spc;
newSD = [newSD; i];
continue;
end
end
SDmap{i} = spc;
toRemove = [toRemove; i];
end
SDmap(toRemove) = [ ];
for i=1:length(newSD)
a = find(toRemove < newSD(i));
newSD(i) = newSD(i)-length(a);
end
end
%================================================================
======
% get the maximum correlation of an SPC with each template
function [cc, idx, spcWave, amps, maxTemplate] = getMaxCorrelation(buf, templates,
bufFs,↓
    threshold, useGPU)
dur=4*60;
tempBuf = [ ];
tempLengths = [ ];
tempOffsets = [ ];
for i=1:length(templates)
temp = templates {i};
if temp.samplingRate > bufFs
ds = temp.samplingRate/bufFs;
tWave = downsample(double(temp.wave), ds);
pnt = round(double(temp.wavePoints)/ds);
sWave = buf;
fs = bufFs;
rng = (0:dur*fs-1)+1 - dur/2*fs + pnt(2);
if (rng(end) > length(tWave))
rng = rng - (rng(end)-length(tWave));
elseif rng(1) < 1
rng = rng-rng(1)+1;
end
N = length(tWave);
```

```
tWave = tWave(rng);
elseif temp.samplingRate < bufFs
ds = bufFs/temp.samplingRate;
sWave = downsample(buf, ds);
tWave = double(temp.wave);
pnt = round(double(temp.wavePoints));
fs = temp.samplingRate;
rng = (0:dur*fs-1)+1 - dur/2*fs + pnt(2);
if (rng(end) > length(tWave))
rng = rng - (rng(end)-length(tWave));
elseif rng(1) < 1
rng = rng-rng(1)+1;
end
N = length(tWave);
tWave = tWave(rng);
else
fs = temp.samplingRate;
sWave = buf;
tWave = double(temp.wave);
N = length(tWave);
pnt = round(double(temp.wavePoints));
end
RNG{i} = rng;
PNT{i} = pnt;
SWAVE{i} = double(sWave);
TWAVE{i} = double(tWave);
tempOffsets = [tempOffsets; int32(length(tempBuf))];
tempBuf = [tempBuf; single(tWave(:))];
tempLengths = [tempLengths: int32(length(tWave))];
end
if useGPU > 0
[maxCorr, maxCorrIdx] = templateCorrelation_gpu(buf, tempBuf, tempLengths,...
tempOffsets, length(templates));
maxCorr = gather(maxCorr);
maxCorrIdx = gather(maxCorrIdx);
else
maxCorr = zeros(length(templates),1);
maxCorrIdx = maxCorr;
parfor i=1:length(templates)
maxCorr(i) = 0;
maxCorIdx(i) = 0;
N = length(TWAVE{i});
for s=1:length(SWAVE{i})-length(TWAVE{i})
range = s + (0:N-1);
sw = SWAVE{i}(range);
cc = corr(sw, TWAVE{i});
if abs(cc) > abs(maxCorr(i))
maxCorr(i) = cc;
maxCorrIdx(i) = s;
end
end
end
end
[cc, maxTemplate] = max(abs(maxCorr));
if (abs(cc)) < threshold
spcWave = [ ];
idx = [ ];
cc = [ ];
amps = [ ];
maxTemplate = [ ];
return;
end
cc = maxCorr(maxTemplate);
idx = maxCorrIdx(maxTemplate);
N = length(TWAVE{maxTemplate});
spcWave = SWAVE{maxTemplate}(double(RNG{maxTemplate})+double(idx));
pnt = PNT{maxTemplate}- (N-length(RNG{maxTemplate}))/2;
if pnt(1) < 1
pnt(1) = 1;
end
if pnt(end) > length(spcWave)
pnt(end) = length(spcWave);
end
amps = spcWave(pnt);
end
%===================================================================
% get the ratio of power depression preceding and following an SPC
% these points are determined by the template
```

```
function spc = checkDepression(spc, pBuffer, corrBufSize)
if ~(spc.corrTested && ~spc.deprTested)
return;
end
pnts = spc.templatePoints;
rng1 = (length(pBuffer) - corrBufSize + spc.corrIdx + pnts(1)) - (0: 120*spc.fs-1);
rng2 = (length(pBuffer) - corrBufSize + spc.corrIdx) + (pnts(2):pnts(3));
P1 = mean(pBuffer(rng1));
P2 = mean(pBuffer(rng2));
spc.P1 = P1;
spc.P2 = P2;
spc.depression = P2/P1;
spc.deprTested = 1;
end
%================================================================
function plotSPC(spc)
figure;
subplot(211);
plot(spc.SPCwave);
subplot(212);
plot(spc.PSD);
end
```

Example 3. Detecting Slow Cortical Potential Changes

Spreading depolarizations (SDs) are transient DC deflections lasting a median of 120-180 seconds, and appear as an EEG waveform as illustrated in FIG. 1. The power spectral density was measured using the Burg autoregressive (AR) estimate. Although other methods may be utilized, AR methods are particularly effective at modeling biosignals such as EEG, and in particular are well-suited for finding frequency domain peaks (described in detail in D. J. Krusienski, et al. "An Evaluation of Autoregressive Spectral Estimation Model Order for Brain-Computer Interface Applications," in *Conference proceedings: Annual International Conference of the IEEE Engineering in Medicine and Biology Society IEEE Engineering in Medicine and Biology Society Conference,* 2006, vol. 1, pp. 1323-1326, D. J. McFarland et al. "Sensorimotor rhythm-based brain-computer interface (BCI): model order selection for autoregressive spectral analysis," *J Neural Eng,* vol. 5, no. 2, pp. 155-162, 2008, and G. Florian et al. "Dynamic spectral analysis of event-related EEG data," *Electroencephalography and clinical neurophysiology,* vol. 95, no. 5, pp. 393-396, 1995. The entire disclosures of these references are incorporated herein by this reference.

In order to determine an appropriate model order, data were first down-sampled to 2 Hz, to eliminate high-frequency signal components that might interfere with modeling low-frequency changes. Then, several initial SD waveforms with 4 minute duration were manually selected from different patient datasets based on varying waveform shape. The means of the waveforms were removed and the power spectral characteristics were determined using Matlab for model orders ranging from 10-100.

Figure 2A:
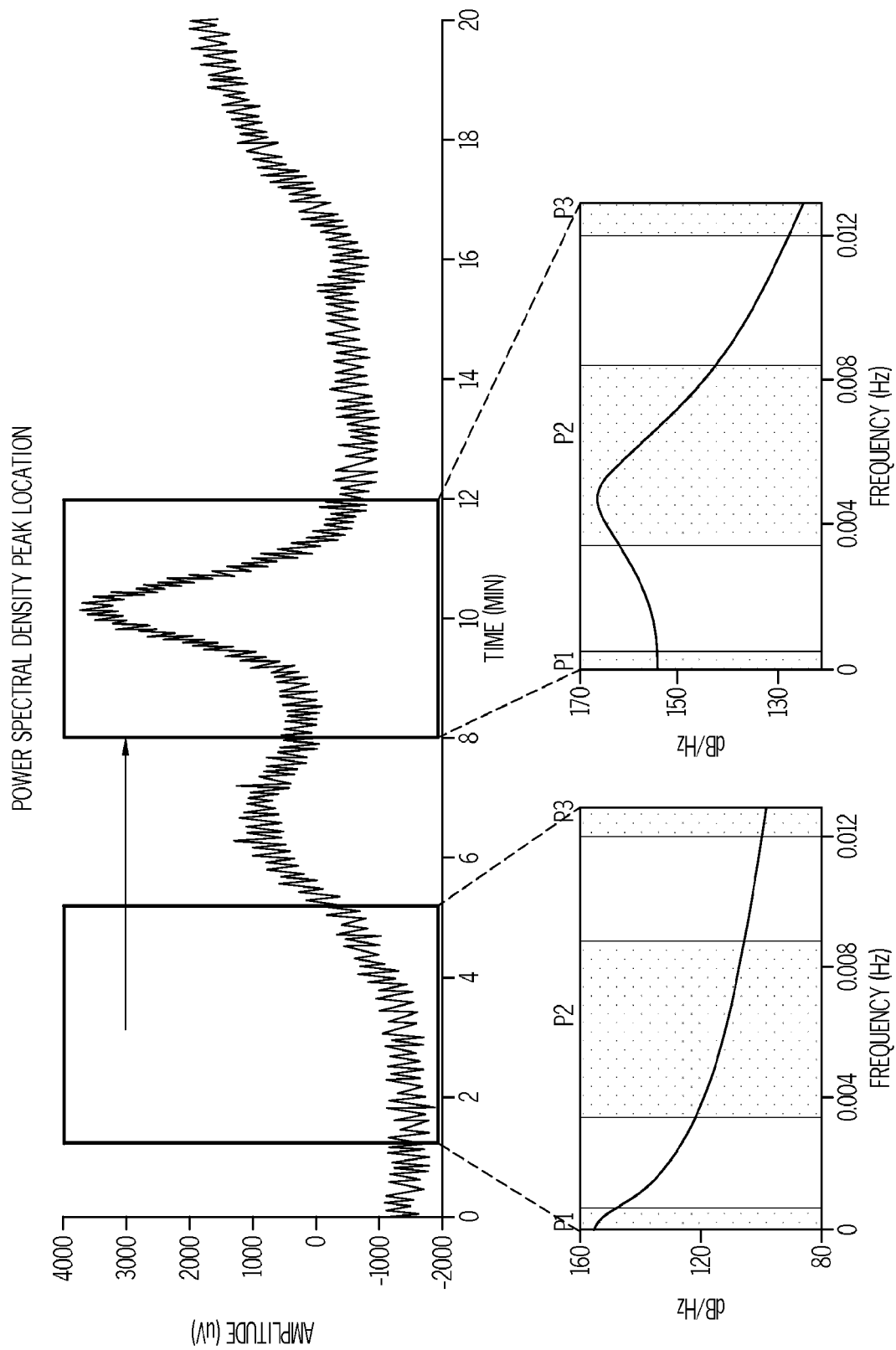
FIG. 2. A) Illustration of determination of power density spectral peak location; B) Illustration of an SD waveform template correlation; C) Illustration of how to calculate amplitude of an SD waveform; D) illustration of an SD high frequency power depression.
Figure 2B:
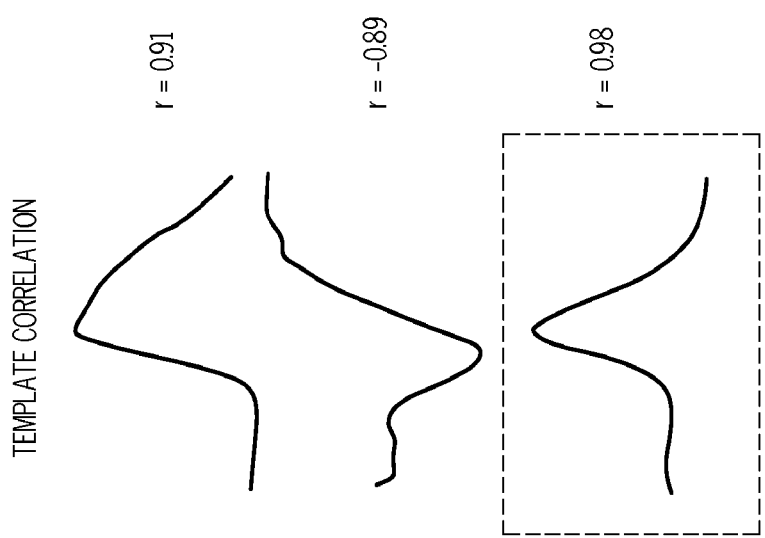
Figure 2B:
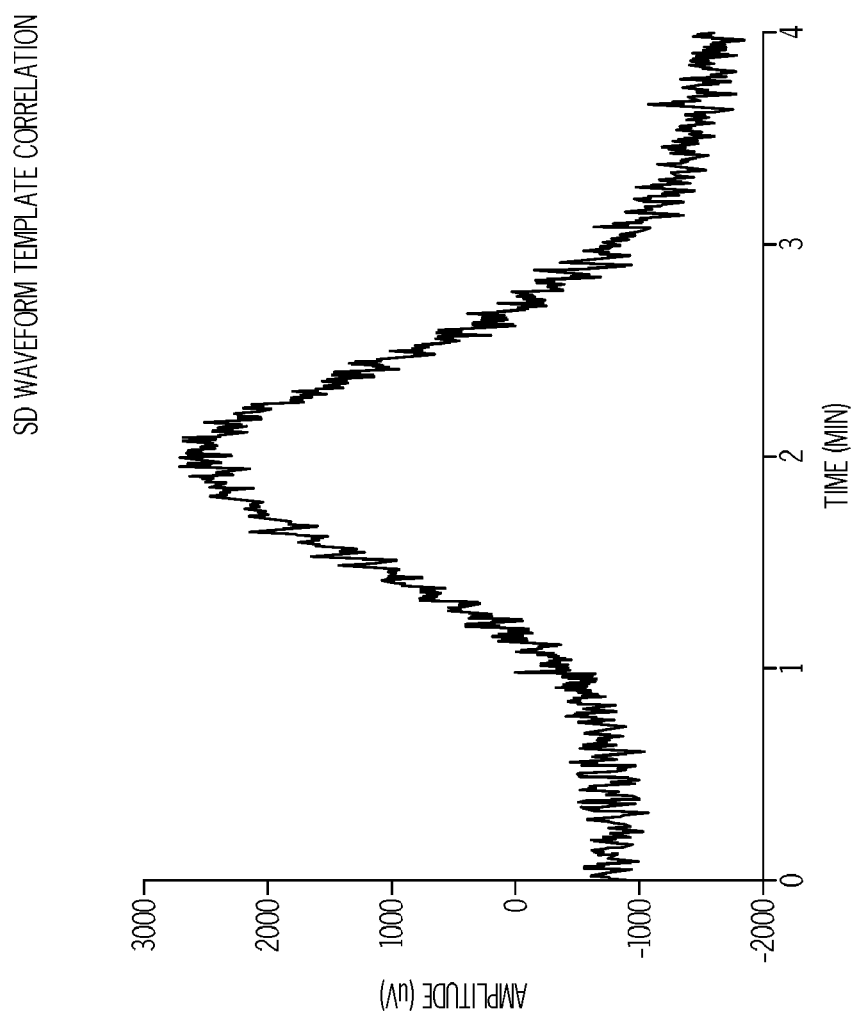

It was found that SD waveforms had peaks between 0.004-0.009 Hz, and these peaks were of greater magnitude than other low-frequency components present in the recordings (FIG. 2A). In all cases, an AR model order of 20 was able to find the peaks in this frequency range. This result corresponds well with an outcome based on the waveform duration; peaks between 0.004-0.009 Hz represent waveforms with a period of 110-250 seconds.

To identify SDs, power ratios were computed by comparing power in the 0.004-0.009 Hz band to power in neighboring lower (0.0-0.001 Hz) and higher (0.012-0.013 Hz) frequency bands. If these ratios, R1 and R2, exceeded 1.5 and 5.0, respectively, events were identified as candidate SDs.

For each candidate SD, a 20 minute data segment centered on the waveform from all 6 EEG channels were saved in an binary data file for further analysis, e.g. SD propagation (see, for example, M. Folk et al. "Hdf5: A file format and i/o library for high performance computing applications," in Proceedings of Supercomputing, 1999, vol. 99, the entire disclosure of which is incorporated herein by this reference).

Example 4. Developing Waveform Templates

Following the initial analysis pass for three patients, representative waveforms were selected from 3 patients to be entered into a waveform template database using a custom graphical program, described in Example 9. A total of 15 waveforms were initially marked. Once the SD waveform templates were entered, the analysis was repeated for all patients. On the second pass of the analysis, when an SD waveform was detected, it was compared to the SD database using a correlation measurement. If the correlation exceeded 0.95, it was marked as a valid SD; otherwise, it was marked as an unlikely SD, but still saved for further potential analysis (e.g., to add it to the database as a valid SD waveform).

Example 5. Amplitude Analysis

Figure 2C:
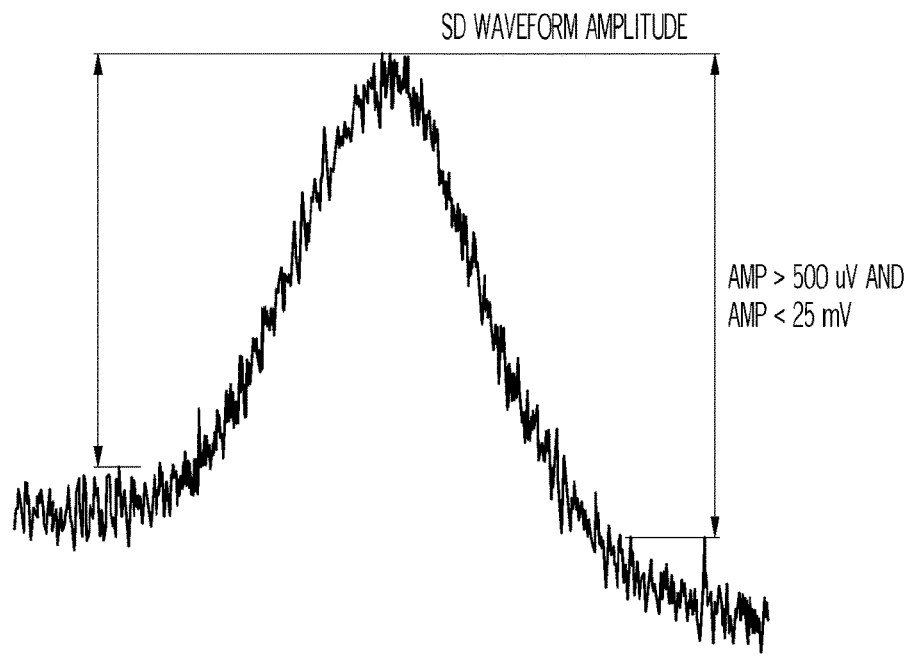
Figure 2D:
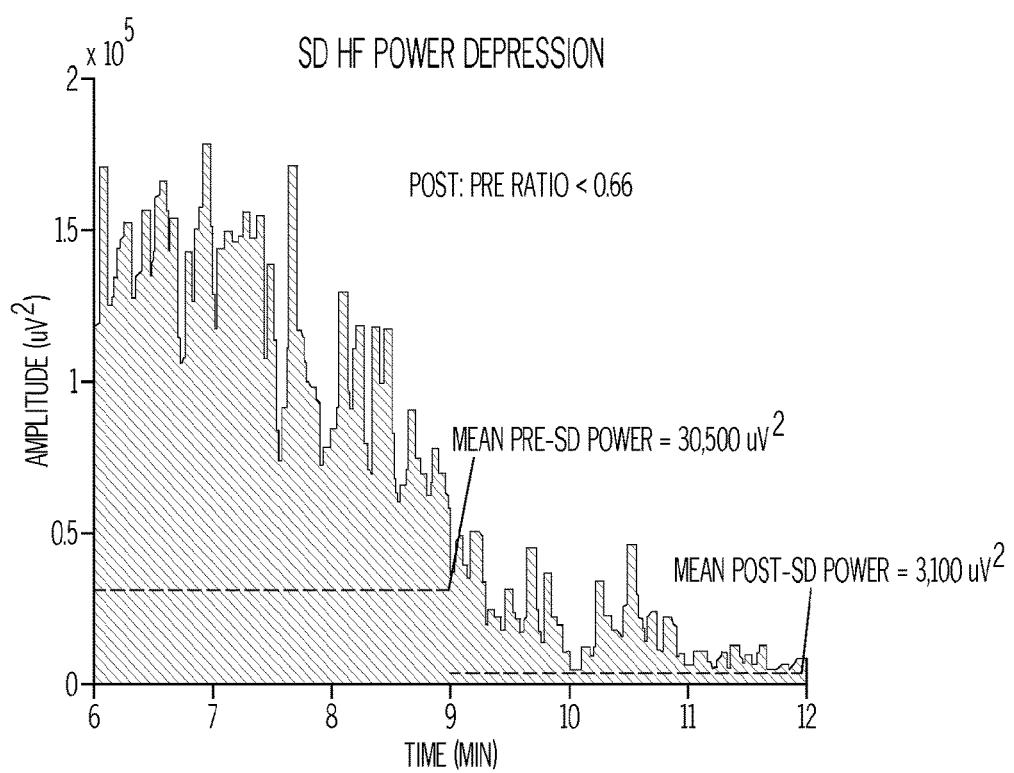
Figure 3:
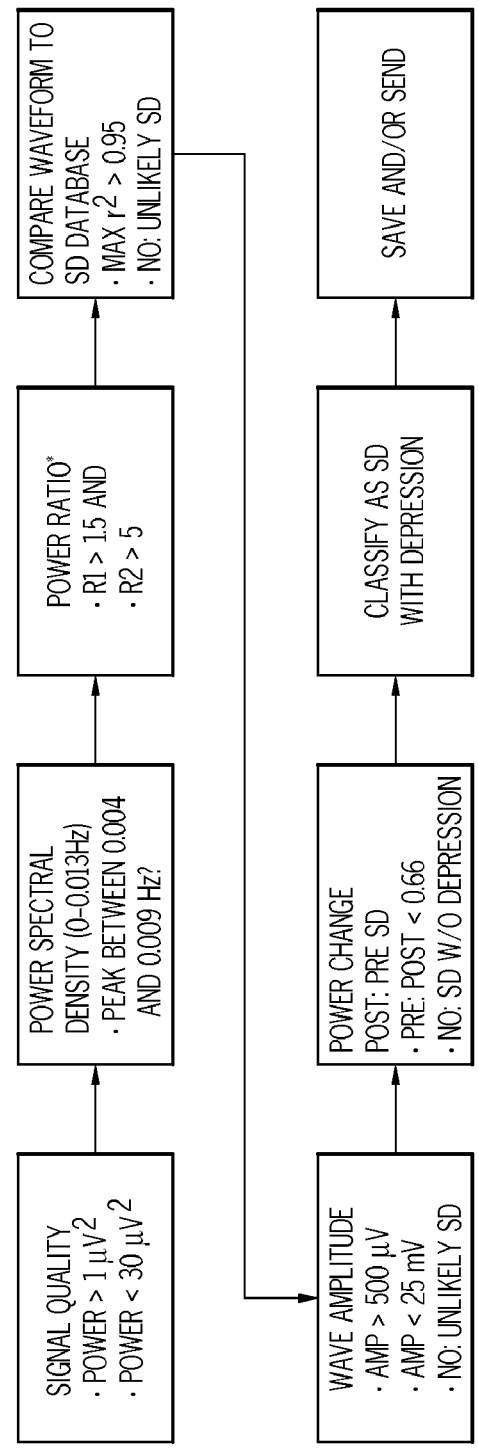
FIG. 3. Flow chart of the automated SD identification algorithm.

The power ratio analysis does not consider the magnitude of the power spectral peaks, and the template correlation analysis compares normalized waveforms. Thus, very large and very small SPCs that may look like SDs may result in false positives. Therefore, the peak-to-peak values of the SD wave are measured to determine if the amplitude is appropriate. A relatively large inclusion window [500 μV-35 mV] was used to allow for system noise, electrode distance from the SD epicenter, and other unknown factors. The SD templates contain time markers for the start, peak, and end of each SD waveform, which were used to determine the amplitude changes; that is, the amplitude from the start marker to the peak marker and from the peak marker to the end marker were each used as separate amplitude measurements (FIG. 2C).

Example 6. High Frequency Power Change

SDs are typically accompanied by depressions in high-frequency activity (>0.5 Hz). Therefore, the mean high-frequency (0.5-100 Hz) power was calculated in a 3 minute window before the first template marker, and in a window after the first template marker. The ratio of the post-marker power and pre-marker power was calculated. If the ratio was <0.66, it was marked as an SD with depression; otherwise, it was marked as an SD without depression. That is, SPCs did not necessarily need to be accompanied by a depression period to be considered an SD. If the total power in a 30 s window exceeds 30 $\mu V^2$ it is marked as noise, rejected as an artifact, and no further analysis is performed.

Example 7. Event Grouping and Propagation

Individual SD events can additionally be examined to determine if the waves propagate, a ubiquitous property of SD. Based on factors that may be unique to a patient, including location and extent of a primary lesion and development age of the patient (infant versus adult, e.g.), a time for propagation determination is selected. According to a specific embodiment, if an SD is detected on a neighboring electrode within 8 minutes, then the two SD's are classified as belonging to the same event, and only the first SD time is used for scoring and real-time notification.

Example 8. Classification Confidence

A classification confidence score is assigned to each SD, based on how many analysis metrics were met. For example, an SPC that had an appropriate frequency domain peak but did not match any templates, had a peak-to-peak amplitude that was too small, did not have depression, and did not propagate would have a very small confidence score. However, an SPC that met all of these criteria would have a high confidence score. In some embodiments, the score can be used as a notification threshold, such that only events with a particular classification confidence will trigger real-time notification, or can be automatically scored without further manual assessment.

Example 9. Spreading Depolarization Analysis Software Tools

Following SD detection, the SD waveform segments were saved in a file for further analysis. SD candidate waveforms were analyzed in a custom software package which reads detected waveform segments from the binary data file, and displays a list of all SD events. The data for all EEG channels are displayed, as well as a zoomed view of the detected waveform and/or high-frequency data (FIG. 4).

Figure 5:
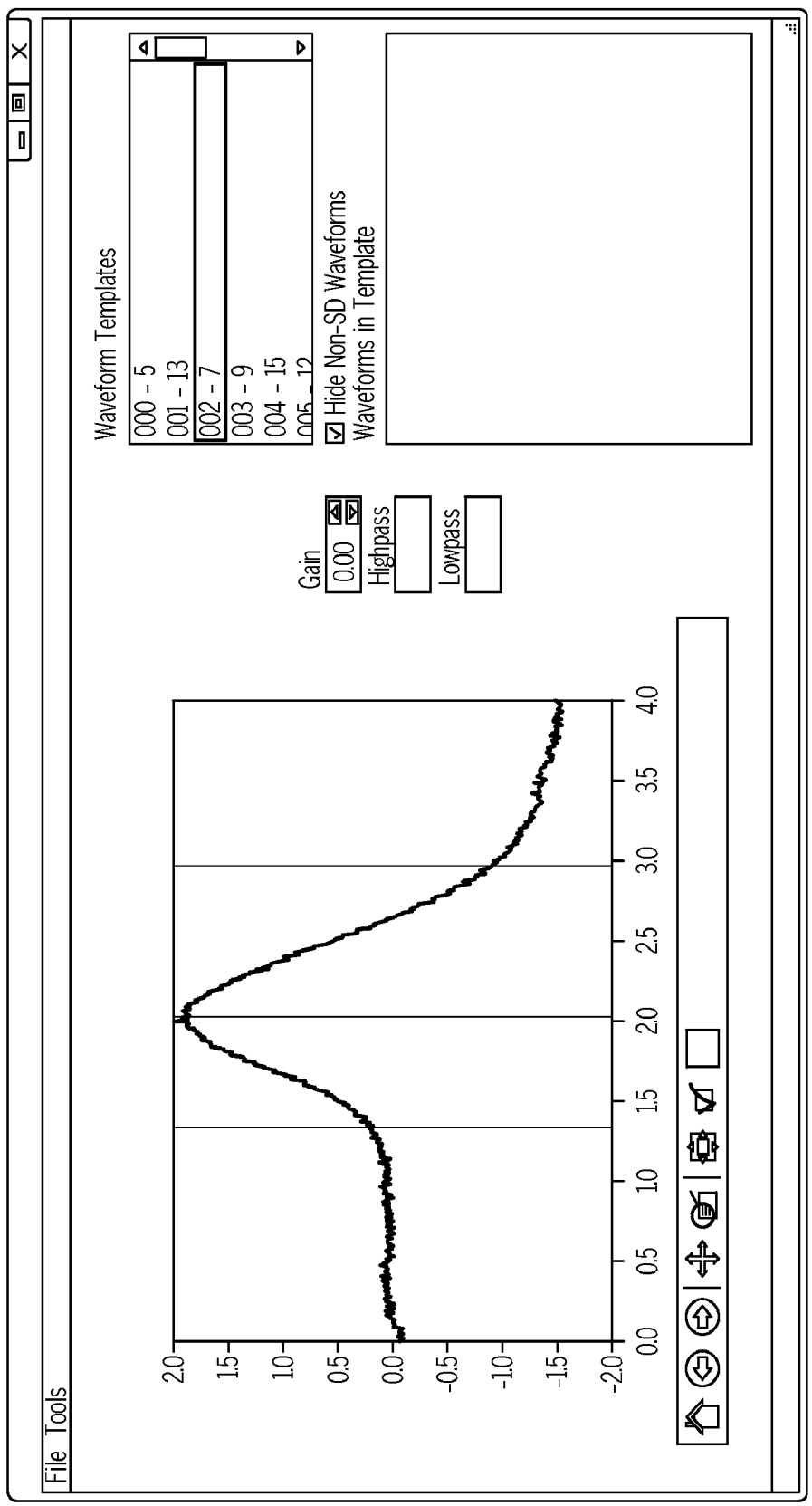
FIG. 5. SD waveform database tool. Illustration of how utility program allows the user to view and edit existing waveforms in the database

The software allows the user to quickly mark waveforms as valid SDs and depressions, classify them as valid or invalid, or otherwise flag them for further analysis. Valid waves may be manually added to the waveform database by clicking on the peak of the wave with the cursor. The new waveform is compared to all waveforms in the database using the correlation. The waveform is then either added to an existing waveform template if the correlation is greater than 0.95, or a new template is created. A utility program allows the user to view and edit existing waveforms in the database (FIG. 5). Within this tool, the waveform corners and peaks are marked with the cursor. This provides a means to measure the amplitude changes specifically for each waveform.

Example 10. Sensitivity and Selectivity

SDs were initially scored by expert visual assessment using LabChart software (ADInstruments) and were considered 'ground truth' for assessing performance of the automated SD detection algorithm. Timestamps of automatically detected events were compared to the timestamps of expert scoring by measuring 1) the time differences between detected and expert-scored events, and 2) the time differences between expert-scored and all detected events. The selectivity was assessed by finding the number of hand-scored SDs that were missed by the algorithm, i.e., the false negative rate. The sensitivity was assessed by finding the number of detected SDs that did not correspond to an expert-scored SD, i.e., the false positive rate.

Some SDs missed in expert scoring are picked up by automatic scoring. Therefore, the SDs that were initially counted as suspected false-positives were manually reassessed to determine if they should have been scored as SD events. After this reassessment, the scoring process was repeated with the updated timestamps, and the updated selectivity and sensitivity were measured again.

Performance of the automated detection algorithm was assessed using the full recording files from the 8 patients used to develop the algorithm. Expert manual scoring of these files identified a total of 497 SDs. Table 1 shows the algorithm performance for each patient. Overall, the sensitivity of the algorithm to detect SDs identified manually was 93% and the selectivity in detecting only events that were manually verified as SD was 85%.

TABLE 1

Table 1 sets forth the selectivity and sensitivity scores for 8 patients. For the Sensitivity, the Detected column contains the number of detected SDs corresponding to a manually identified event and the Scored column contains the total number of manually identified SDs. For the Selectivity, the Scored column contains the number of manually identified SDs corresponding to a SD detected by the algorithm, while the Detected column contains the total number of detected SDs. The FP/hr column gives the # of false-positives per hour, and the hr/FP gives the hours between false positives

| Patient | Recording Time(hr) | Sensitivity | | Selectivity | | | |
|---|---|---|---|---|---|---|---|
| | | | Detected | Scored | Scored | Detected | FP/hr | hr/FP |
| 1 | 143.82 | 93.00% | 104 | 112 | 98.00% | 317 | 322 | 0.03 | 28.76 |
| 2 | 50.96 | 100.00% | 1 | 1 | 54.00% | 7 | 13 | 0.12 | 8.49 |
| 3 | 34.2756 | 0.00% | 0 | 0 | 0.00% | 0 | 0 | 0.00 | 0.00 |
| 4 | 163.29 | 98.00% | 58 | 59 | 94.00% | 339 | 360 | 0.13 | 7.78 |
| 5 | 139.65 | 89.00% | 108 | 122 | 96.00% | 437 | 455 | 0.28 | 3.58 |
| 6 | 149.15 | 95.08% | 116 | 122 | 67.00% | 136 | 203 | 0.45 | 2.23 |

TABLE 1-continued

Table 1 sets forth the selectivity and sensitivity scores for 8 patients. For the Sensitivity, the Detected column contains the number of detected SDs corresponding to a manually identified event and the Scored column contains the total number of manually identified SDs. For the Selectivity, the Scored column contains the number of manually identified SDs corresponding to a SD detected by the algorithm, while the Detected column contains the total number of detected SDs. The FP/hr column gives the # of false-positives per hour, and the hr/FP gives the hours between false positives

| Patient | Recording Time(hr) | Sensitivity | | | Selectivity | | | |
|---|---|---|---|---|---|---|---|---|
| | | | Detected | Scored | Scored | Detected | FP/hr | hr/FP |
| 7 | 164.76 | 98.00% | 47 | 48 | 67.00% | 259 | 385 | 0.76 | 1.31 |
| 8 | 159.65 | 88.00% | 29 | 33 | 68.00% | 65 | 96 | 0.19 | 5.15 |
| Total | 1005.5556 | 93.16% | 463 | 497 | 85.06% | 1560 | 1834 | 0.27 | 3.67 |

Aspects and embodiments of the invention have been set forth in detail in order to provide sufficient guidance to the practitioner to practice the inventive methods and systems as defined by the claims. A person of ordinary skill in the art will understand that other aspects and embodiments exist which are also within the scope of the claims. Where elements are presented as lists, it is to be understood that each subgroup of the elements is also disclosed, and any element(s) can be removed from the group. The invention provides all such embodiments. It should also be understood that, in general, where the invention, or aspects of the invention, is/are referred to as comprising particular elements, features, etc., certain embodiments of the invention or aspects of the invention consist, or consist essentially of, such elements, features, etc.

The terms "approximately" or "about" in reference to a number generally include numbers that fall within ±10%, in some embodiments ±5%, in some embodiments ±1%, in some embodiments ±0.5% of the number unless otherwise stated or otherwise evident from the context (except where such number would impermissibly exceed 100% of a possible value). Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. In addition, any particular embodiment, aspect, element, feature, etc., of the present invention may be explicitly excluded from any one or more of the claims.

The invention claimed is:

1. A non-transitory computer-readable storage medium containing program instructions for causing a computer to perform a method of real-time detection of spreading depolarizations in a brain injured patient, the method comprising:
    (a) providing a reference database of spreading depolarization (SD) waveform templates generated from EEG recordings of confirmed spreading depolarizations in a reference brain-injured patient cohort;
    (b) recording, by an EEG device, an EEG of the brain injured patient to generate recorded EEG waveforms;
    (c) detecting a slow potential change (SPC) present in the recorded EEG waveform by applying a power spectral density estimate to the recorded EEG waveform;
    (d) comparing the detected SPC to the reference database of SD waveform template to identify a candidate SD; and
    (e) rejecting the candidate SD as a false positive based on overall signal power and amplitude analysis and identifying a non-rejected candidate SD as a detected SD.

2. The non-transitory computer-readable storage medium according to claim 1, wherein the method further comprises:
    (f) testing a detected SD for depression of high-frequency power and identifying a detected SD as an SD with depression if depression of high-frequency power is observed, wherein high-frequency is frequency greater than 0.5 Hz.

3. The non-transitory computer-readable storage medium according to claim 1, wherein the power spectral density estimate according to step (c) comprises an autoregressive power spectral density estimate based on selection of a model order of about 20.

4. The non-transitory computer-readable storage medium according to claim 1, wherein total signal power is between 1 µV2 and 30 µV2 across a 30 second window, and if the total signal power is greater than 30 µV2 then no further analysis is performed within the 30 second window.

5. The non-transitory computer-readable storage medium according to claim 1, wherein the recorded EEG waveform is identified as a detected SPC according to (c) if, upon application of the AR power spectral density estimate, the recorded EEG waveform exhibits a peak between 0.004 Hz and 0.009 Hz, within a period of 110-250 seconds, said peak having a peak power, a power ratio R1>1.5 and a power ratio R2>5, wherein R1 is a ratio of the peak power to power in a neighboring lower frequency band and R2 is a ratio of the peak power to power in a neighboring higher frequency band.

6. The non-transitory computer-readable storage medium according to claim 1, wherein comparing according to (d) comprises calculating a coefficient of correlation between the detected SPC and the reference waveform database template and scoring the detected SPC as a candidate SD if r2>0.95.

7. The non-transitory computer-readable storage medium according to claim 6, wherein the candidate SD is rejected as a false positive if a calculated peak-to-peak value of the candidate SD is measured as less than 500 µV or greater than 35 mV.

8. The non-transitory computer-readable storage medium according to claim 2, wherein (f) comprises: (i) calculating a mean high-frequency power in a time frame prior to a template marker; (ii) calculating a mean high-frequency power in a time frame subsequent to the template marker; (iii) calculating a ratio of (i) to (ii); and (iv) identifying the detected SD as a detected SD with depression if the ratio is <0.66.

9. The non-transitory computer-readable storage medium according to claim 1, wherein the EEG is intracranial EEG or scalp EEG.

10. The non-transitory computer-readable storage medium according to claim 2, wherein he detected SD is further analyzed for propagation, the method comprising: (g) detecting an SD on a neighboring electrode and classifying the detected SD and the detected neighboring SD as propagating from a same event if the detected neighboring SD occurs within eight (8) minutes of the detected SD.

11. The non-transitory computer-readable storage medium according to claim 2, wherein each detected SD is assigned a confidence classification and one or more notification thresholds are set for notifying a clinician of the detected SD, said thresholds set according to a confidence classification.

12. The non-transitory computer-readable storage medium according to claim 1, further comprising adding waveforms for the detected SD into the reference database.

13. An automated clinical method for rapid triage of brain-injured patients by detecting spreading depolarizations, the method comprising: effectuating the automated algorithm according to claim 10 and assigning a greater urgency to patients exhibiting a detected SD over patients not exhibiting a detected SD, and a greater urgency to patients exhibiting a propagating SD over patients not exhibiting a propagating SD.

14. The automated clinical method according to claim 13 having a sensitivity for detecting a verified spreading depolarization of greater than 90% and a selectivity for detecting a verified spreading depolarization of greater than 80%.

* * * * *